Feb. 8, 1944. W. I. JOHNSTON Plant Pat. 614
ROSE PLANT
Filed Sept. 15, 1943
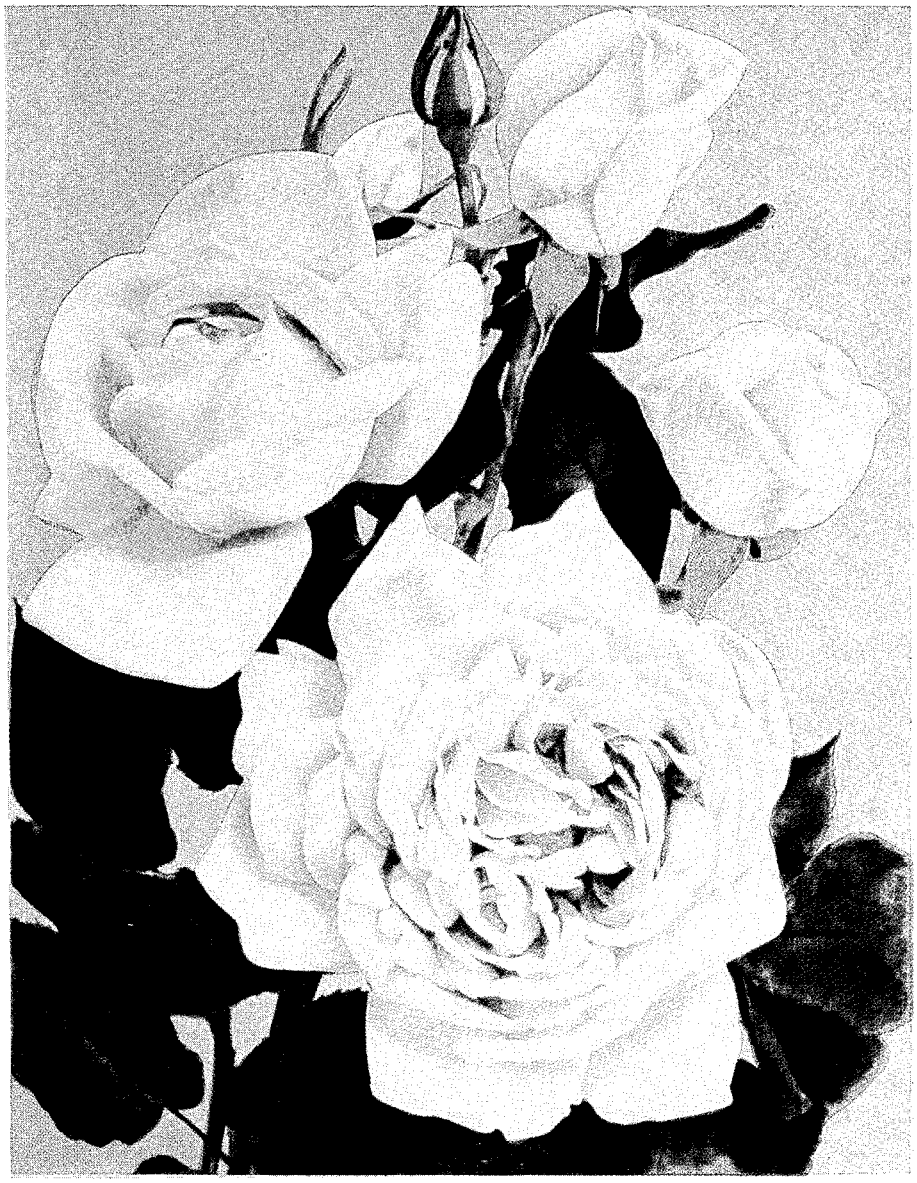
Inventor
W. I. Johnston
By Robert Robb
Attorney Patented Feb. 8, 1944

Plant Pat. 614

UNITED STATES PATENT OFFICE

614

ROSE PLANT

Walter Irwin Johnston, Portadown, Ireland, assignor to Jackson & Perkins Company, Newark, N. Y., a corporation of New York Application September 15, 1943, Serial No. 502,523

1 Claim. (Cl. 47—61)

The present invention relates to a new and distinct variety of rose plant, originated by crossing "Mrs. A. R. Barraclough" with an unnamed seedling, having as a primary objective to improve upon the seed parent. "Mrs. A. R. Barraclough" is a tall, vigorous growing rose of a Carmine Pink with a pointed bud, but it has a decided drawback in that the stems are very pithy and the flowers, therefore, do not keep well. By cross breeding as above stated, not only was this defect entirely eliminated, but I obtained a flower of an unusual color combination and further distinguishing from the seed parent by not having the tall upright growth.

This color combination arises by virtue of the fact that the inside of the petals are of a color between Deep Rose and Thulite Pink while the reverse of the petals is a Pale Vinaceous-Lilac undertone overlaid with Cameo Pink and suffused with Light Buff at the base. Such coloring is not found in either of the parents or other roses, so far as I am aware.

Along with this novel coloring, this new flower is characterized by its large size and fine balance as clearly illustrated in the accompanying drawing.

This new variety discloses a further feature of novelty in respect to its Jade Green oval-pointed double serrated foliage.

Asexual reproduction shows that these characteristics hold true through succeeding propagations.

The following is a detailed description of this new variety, color terminology being in accord with Ridgway's Color Standard:

Parentage: Seedling.
- *Seed parent.*—"Mrs. A. R. Barraclough."
- *Pollen parent.*—Unnamed seedling.

Classification: Botanic and commercial—hybrid tea.

*Flower*

(Observations made in the fields of Jackson & Perkins Company, Newark, New York, in the morning of September 27, 1942.)

Blooming habit: Recurrent—continuous.

Bud:
- *Size.*—Medium.
- *Form.*—Ovoid. Is not affected by wet or hot weather.
- *Color.*—When sepals first divide—Rose Color, Plate 12. When petals being to unfurl—Spinel Pink, Plate 26. When half blown: inside of petals—Spinel Pink, Plate 26, overcast with Thulite Pink, Plate 26. Reverse of petals—Pale Vinaceous-Lilac, Plate 44, overlaid with Rose Pink, Plate 12, with a reflection of Naphthalene Yellow, Plate 16, from the base of the petal.
- *Sepals.*—Serrated, "hood" above bud. Curl back when petals begin to unfurl.
- *Color:* outside—Lettuce Green, Plate 5; inside—Pale Yellow Green, Plate 6.
- *Calyx.*—*Shape*—pear. *Size*—long. *Aspect*—smooth. *Color*—Oil Green, Plate 5.
- *Peduncle.*—*Length*—short. *Aspect*—smooth. *Color*—Oil Green, Plate 5. *Strength*—erect; slender.
- *Opening.*—Bud opens well. Is not affected by adverse conditions.

Bloom:
- *Size.*—Large. Average size when fully expanded, four inches.
- *Borne.*—Singly.
- *Stems.*—Medium length; strong.
- *Form.*—When first open—cupped. Permanence—Retains its form to the end.
- *Petalage.*—Double (full but open center). Number of petals under normal conditions, 30.
- *Color.*—Center of flower—Deep Rose Pink, Plate 12. Outer petals—between Deep Rose Pink, Plate 12, and Thulite Pink, Plate 26. Base of petals (aiglet)—Pinard Yellow, Plate 4. Inside of petals—between Deep Rose Pink, Plate 12, and Thulite Pink, Plate 26. Reverse of petals—Pale Vinaceous-Lilac, Plate 44, overlaid with Cameo Pink, Plate 26, and with a reflection of Light Buff, Plate 15, at the base. General tonality from a distance—Deep Rose Pink, Plate 12.
- *Discoloration.*—General tonality at end of first day—Deep Rose Pink, Plate 12. Second day—between Deep Rose Pink, Plate 12, and Rose Pink, Plate 12. Third day—Rose Pink, Plate 12.

Petals:
- *Texture.*—Leathery. Is not affected by wet or hot weather.
- *Appearance.* — Inside — velvety. Outside—shiny.
- *Form.*—Oval; notched.
- *Arrangement.*—Irregular. Petaloids in center—few; small.
- *Persistence.*—Drop off cleanly.
- *Fragrance.* — Strong. Nature — "Old Rose perfume" (Centifolia).
- *Lasting quality.*—On the plant as cut flower—long.

Genital organs:

*Stamens, anthers.*—Medium size; many. *Color*—Light Cadmium, Plate 4. *Arrangement*—regular around styles.

*Stamens, filaments (threads).*—Long. *Color*—Apricot Yellow, Plate 4.

*Pollen.*—Buff Yellow, Plate 4.

*Styles.*—Loosely separated, uneven length; medium length; thin.

*Stigmas.*—Capucine Buff, Plate 4.

*Ovaries.*—Some protruding from calyx.

*Plant*

Form: Bush.

Growth: Vigorous; branching.

Foliage: 5 leaflets.

*Size.*—Large.

*Quantity.*—Abundant.

*Color.*—New foliage: upper side—Lettuce Green, Plate 5, overlaid with Madder Brown, Plate 13; under side—Van Dyke Red, Plate 13. Old foliage: upper side—Jade Green, Plate 31; under side—Light Cress Green, Plate 31.

*Shape.*—Oval-pointed.

*Texture.*—Upper side—Glossy; under side—rough. Ribs and veins—ordinary.

*Edge.*—Serrated.

*Serration.*—Double; sharp.

*Rachis.*—*Color*—Cress Green, Plate 31. Under side—smooth.

*Stipules.*—Long; bearded.

*Disease resistance.*—Resistant insofar as this is evidenced by absence of any disease throughout development and establishment of this variety.

Wood:

*New wood.*—*Color*—Lettuce Green, Plate 5. *Bark*—smooth.

*Old wood.*—*Color*—Dark Cress Green, Plate 31. *Bark*—smooth.

Thorns: (thorns are divided into thorns, prickles and short needles):

*Thorns.*—On main stalks from base—few; on laterals from stalk—none. Form—Narrow base; short; hooked downward. Color when young—Madder Brown, Plate 13. Position—irregular.

*Prickles.*—On main stalks and on laterals—none.

*Short needles.*—On main stalks and on laterals—none.

I claim:

A new and distinct variety of rose plant, characterized as to novelty by the unusual color combination of its flowers, growing upon non-pithy branching stems; the large size and excellent balance of form of these flowers; and the Jade Green oval-pointed double serrated foliage, substantially as shown and described.

WALTER IRWIN JOHNSTON.